United States Patent
Porzelt et al.

(10) Patent No.: US 8,103,014 B2
(45) Date of Patent: Jan. 24, 2012

(54) HEARING PROTECTOR FOR USE IN MAGNETIC RESONANCE SYSTEMS

(75) Inventors: Klaus Porzelt, Nürnberg (DE); Günter Schnur, Hemhofen (DE)

(73) Assignee: Siemens Aktiengesellschaft, Munich (DE)

( * ) Notice: Subject to any disclaimer, the term of this patent is extended or adjusted under 35 U.S.C. 154(b) by 497 days.

(21) Appl. No.: 12/378,206

(22) Filed: Feb. 12, 2009

(65) Prior Publication Data

US 2009/0208029 A1    Aug. 20, 2009

(30) Foreign Application Priority Data

Feb. 15, 2008 (DE) .......................... 10 2008 009 187
Aug. 14, 2008 (DE) .......................... 10 2008 037 818

(51) Int. Cl.
*A61F 11/06* (2006.01)
(52) U.S. Cl. .......................................... 381/72; 381/380

(58) Field of Classification Search ................... 381/72, 381/380, 382; 181/131; 600/418
See application file for complete search history.

(56) References Cited

U.S. PATENT DOCUMENTS

| 5,631,965 | A | 5/1997 | Chang et al. | |
|---|---|---|---|---|
| 7,609,844 | B2 * | 10/2009 | Lederer | 381/380 |
| 2003/0112985 | A1 | 6/2003 | Baumbart et al. | |
| 2004/0086138 | A1 | 5/2004 | Kuth | |
| 2005/0197565 | A1 | 9/2005 | Yagi et al. | |

FOREIGN PATENT DOCUMENTS

| DE | 10112305 A1 | 10/2002 |
|---|---|---|
| DE | 10251389 A1 | 5/2003 |
| DE | 102004059678 A | 12/2004 |
| DE | 10324763 A1 | 1/2005 |
| DE | 10343006 A1 | 4/2005 |

* cited by examiner

*Primary Examiner* — Mark Prenty

(57) ABSTRACT

The invention relates to a hearing protector for use in magnetic resonance systems. The hearing protector comprises a pad that is to be inserted in the ear and is provided on an adapter. A sound generating device is provided on or in the adapter or a sound transmitting device leads into same.

12 Claims, 3 Drawing Sheets

HEARING PROTECTOR FOR USE IN MAGNETIC RESONANCE SYSTEMS

CROSS REFERENCE TO RELATED APPLICATIONS

This application claims priority of German application No. 10 2008 009 187.1 filed Feb. 15, 2008. The application also claims priority of German application No. 10 2008 037 818.6 filed Aug. 14, 2008. Both of the applications are incorporated by reference herein in their entirety.

FIELD OF THE INVENTION

The invention relates to a hearing protector for use in magnetic resonance systems.

BACKGROUND OF THE INVENTION

It is well-known that during the operation of a magnetic resonance system a considerable level of noise is generated due to equipment-related operational factors. A patient undergoing examination by means of a magnetic resonance system must therefore wear a hearing protector, it being necessary to ensure in this case that the volume level at the entrance to the patient's ear (auditory canal) does not exceed 99 dBa.

A known hearing protector, often also referred to as a cap-type ear defender, consists of two ear covers that typically fit closely to the ear, or to the head around the ear, by way of padding. The covers are connected to each other via a clip which can be telescoped such that the hearing protector can be adjusted to the wearer's head size and are usually pivotably attached to the clip. Known covers consist of a hemispherical or dome-shaped, outward-curving plastic outer shell inside which there is arranged a thin inlay of foam material, the annular surface padding being arranged in the area of the shell pointing toward the head. The curvature of the generally oval outer shell is usually not symmetrical, said outer shell instead curving further outward in the lower section, which is further from the clip, than in the upper section.

A hearing protector of said kind which has a considerable width due to its design can be used in a number of examinations in which magnetic resonance systems are used because there are no space problems. In the case of examinations in the head and neck region, however, it is necessary to position special surface coils, called head coils or head-neck coils, on the patient in order to enable meaningful magnetic resonance images to be recorded. The coils, which are normally designed in the form of a cage, must be arranged as close as possible to the head of the patient in this case. A hearing protector of the type cited in the introduction cannot be used in such cases since it often cannot be worn in an appropriate manner or the coil cannot be properly positioned.

A hearing protector suitable for use in this case, implemented in the manner of headphones with a clip, is known from the German patent application 10 2004 059 678. Said hearing protector is characterized in that arranged in the plastic outer shell and permanently joined thereto is a solid inner part which consists of a dimensionally stable plastic composition and fills out the outer shell, the outer shell preferably being filled completely. Said known hearing protector is relatively slim, in other words does not bulge out too much at the sides, and offers very good acoustic insulation since the outer shell is completely filled out by the inner part.

Nonetheless, said hearing protector is likewise implemented in the manner of a headset, with the two ear covers being positioned on the outside of the ears or head, with the overall result that there is still an increase in the size of the volume to be encompassed by the head or head-neck coil due to the hearing protector being fitted.

SUMMARY OF THE INVENTION

The invention is therefore directed toward the problem of disclosing a hearing protector which enables measuring coils to be positioned virtually up to immediate proximity to the head.

In order to solve said problem it is inventively provided in the case of a hearing protector of the type cited in the introduction that a pad which is to be inserted in the ear is provided on an adapter, wherein a sound generating device is provided on or in the adapter or a sound transmitting device leads into same.

The hearing protector according to the invention takes the form of an in-ear headphone, which is to say that it is inserted with the ear pad into the ear or auricle and fixed in the ear or auricle by means of the malleable ear pad, the latter typically consisting of a foam material. The ear pad is provided on an adapter which in turn has a sound generating device which can be controlled from outside and generates sound waves that are actively to be transmitted. Alternatively, a sound transmitting device in the form of a thin tube can also lead to the adapter, sound waves generated by an external sound source being directed to the adapter via said tube.

The adapter itself is very small, since in the end its sole function is to fix the ear pad in place as well as either to house a very compactly built sound generating device itself or simply to be connected to a sound transmitting device, in other words, for example, the thin tube. This means that the entire hearing protector—of which, of course, two are to be used during operation, one in each ear—is very compact in design and is fixed in place in the ear, and in the wearing position projects only slightly beyond the head geometry. As a result there are no space problems whatever with regard to the positioning of a head coil or head-neck coil, since the two hearing protectors stand out from the head only to a negligible extent on each side. Nonetheless, the direct arrangement of the hearing protector or, as the case may be, ear pad together with a part of the adapter in the ear or in the auricle ensures very good acoustic insulation.

In contrast to all previously known hearing protector embodiments which are typically connected to a tube supply line via which corresponding signals or information are transmitted by means of an external sound generating device, in the case of the hearing protector according to the invention a self-contained sound generating device is provided directly integrated into the adapter. The adapter, which is very small and only a few millimeters to centimeters large, can consequently accommodate a very small sound generating device which, in view of the fact that the adapter is situated in immediate proximity to the ear, is nevertheless perfectly adequate for generating easily distinguishable sound signals.

According to a first embodiment of the invention, a sound generating device of said kind can consist simply of a controllable coil that is connected to an oscillating membrane. Said coil, which is operated from outside by way of external control lines, is connected to the oscillating membrane. A permanent magnet core as contained in conventional sound generating devices is not provided in this case. Said magnet core would also be a source of interference in the course of the magnetic resonance imaging. Nonetheless, said sound generating device works exceptionally well when the hearing protector is worn during the examination, since the magnetic field generated by the permanent magnet in the case of conventional sound generating devices is provided according to the invention by the base magnetic field, usually also referred to as the B0 field, of the base field magnet of the magnetic resonance device. It has transpired in this case that said base magnetic field is perfectly adequate for ensuring the operability of the sound generating device consisting simply of coil and oscillating membrane. Surprisingly, it is also not particularly significant in this case how the base magnetic field, which is a static magnetic field with a defined field direction, stands relative to the coil axis or coil spatial coordinates, for due to the multidimensional coil embodiment there is always a small field component which has a sufficient field vector that is adequate for the active movement of the membrane. This means that with such a simply constructed sound generating device in conjunction with the base magnetic field that is present anyway it is possible to integrate into the small adapter a sound generating device which enables sound signals to be generated that are exceptionally distinguishable and extend over a wide frequency range.

The coil itself can be an annular coil having one or more turns or a flat coil lying in a single plane and configured in, for example, a meander-like shape. In any case the coil is directly connected to the oscillating membrane. The alternating magnetic field generated by the coil has proved a source of little interference with regard to the magnetic resonance imaging since it is very low, not least because of the very small coil geometry and the very small control currents. In view of the fact that the hearing protector according to the invention allows excellent positioning of the measuring coils, the minimal field interferences resulting from the operation of the sound generating device are essentially tolerable.

Nonetheless, when a coil of said kind is used it can also happen that image artifacts are produced in many cases. In a beneficial further embodiment of the present invention it can therefore be provided that at least one permanently mounted compensation coil is provided on or in the adapter for the purpose of compensating for a magnetic field generated by the coil. It is therefore proposed to neutralize the field generated by the coil during the sound generation again by means of a compensation coil or a compensation coil arrangement which is embodied accordingly. In concrete terms it can then be provided, for example, that the compensation coil, which is identical in design to the coil, is arranged axially adjacent to the coil and can be inversely supplied with current. Accordingly, when an annular coil is used, an annular coil is also provided as the compensation coil, which annular coil is axially adjacent as closely as possible to the coil connected to the oscillating membrane. If a flat coil is used, then a further flat coil of said kind is positioned congruently parallel thereto as closely as possible to the flat coil connected to the annular membrane. In this case, in order to achieve an ideal compensation during inverse supplying of current, the gap should be chosen such that there is just no contact between the coil and the compensation coil when the oscillating membrane is at its maximum deflection. Alternatively, it can also be provided that the compensation coil embodied as an annular coil of smaller or larger diameter than that of the coil embodied as an annular coil is arranged coaxially with respect to the coil at least partially inside the coil or enclosing the coil and can be inversely supplied with current. In a design of such a kind a difference in the diameter is accepted in order to enable the coil and the compensation coil to be placed even more closely adjacent to each other. In order to ensure that the two annular coils can overlap as completely as possible it can be provided that the oscillating membrane has a shape which bulges out in the center and/or that the coil is connected to the oscillating membrane via a spacer ring. Both embodiments, the first being beneficial for a compensation coil inserted into the coil, allow a maximally congruent arrangement of the annular coils, without the risk of a contact occurring between the oscillating membrane and the compensation coil or the compensation coil and the coil in the event of oscillations of the oscillating membrane. The exemplary embodiments of compensation by means of a compensation coil that are cited here are of course only to be understood as examples: arrangements of arbitrary complexity are conceivable which permit a compensation of the field generated by the coil connected to the oscillating membrane on the basis of, for example, model calculations. In this case the compensation coil should, as described, be fixedly mounted, in other words not be capable of oscillations. Toward that end the compensation coil can be secured on the adapter by way of, for example, a carrier element; it is, however, also conceivable for the compensation coil or the compensation coils to be molded into the adapter. The use of a compensation coil has the advantage generally that interferences with the magnetic resonance measurement are even more extensively prevented. The occurrence of artifacts is avoided. In one embodiment having a compensation coil through which a current flows inversely and which is disposed as close as possible to the coil, all that remain are quadrupole-like stray magnetic fields which have only a very small range, which means that the field strength of said stray magnetic field decreases very rapidly as the distance from the coils increases. A further advantage results owing to the repelling force between the coil connected to the oscillating membrane and the static compensation coil, for by this means the resonance or, as the case may be, efficiency of the oscillating membrane can be improved. Moreover, said repelling force is also effective outside the magnetic field of the magnetic resonance system.

An alternative to the use of a coil together with oscillating membrane as a sound generating device provision is made for the use of a controllable piezoelectric transducer which itself serves as an oscillating membrane. Said piezoelectric transducer consists of two very thin metal surfaces which are connected to corresponding brought-out control lines and which between them accommodate a very thin, membrane-like layer made of a piezoelectric material. The metal layers are applied to the piezoelectric intermediate layer e.g. by vapor deposition. The piezoelectric material deforms as a function of an applied voltage. This means that an oscillation of said piezoelectric transducer can be generated by corresponding control or application of voltage signals, said oscillation serving to generate sound. This sound generating device is also very small, which is to say that it does not have an interfering effect on the magnetic resonance imaging. Only the metal surfaces form sources of interference, which, though, in view of the extremely small surface area of only a few square millimeters, are likewise negligible, not least because in this case, too, only very small control currents are applied. Exceptionally distinguishable sound signals can also be generated with a piezoelectric sound generating device of said kind.

Both in the case of a sound generating device having a coil and in the case of a piezoelectrically operating sound generating device, the arrangement of one or more sheath wave absorbers in a control line leading to the respective sound generating device is necessary in order to avoid the high-frequency field requiring to be applied for recording a magnetic resonance image being decoupled via the control line and preventing field enhancements in the examination region.

As an alternative to the direct integration of a sound generating device into the adapter itself it is possible to lead a tube connection to the adapter as a sound transmitting device and connect it to said adapter, which tube connection is connected to an external sound generating device. In this case, therefore, a pneumatic sound transmission takes place, with the sound waves being generated by an external sound generating device, in other words a corresponding transducer.

The ear pad itself is fixed in place, preferably detachably, on the outside of the adapter, which fixing can be realized without difficulty by means of a simple force fit or a slight latch fit. This enables the ear pad to be easily replaced, not least for reasons of hygiene.

According to a first inventive alternative the adapter itself has an essentially cylindrical shape, with the adapter being accommodated for up to at least a third of its length in the ear pad, which means that the adapter is itself partially situated in the ear or auricle when being worn. As an alternative to an elongate embodiment variant, the adapter can also have an angled shape, with the ear pad being detachably inserted onto an angled retaining section.

Regardless of whether the adapter is now implemented as elongate or angled, it is basically possible to embody it in a very small design, which is possible not least because the active sound generating devices in particular can also be designed very compactly and therefore integrated.

BRIEF DESCRIPTION OF THE DRAWINGS

Further advantages, features and details will become apparent from the exemplary embodiments described below as well as with reference to the drawings, in which.

DETAILED DESCRIPTION OF THE INVENTION

Figure 1:
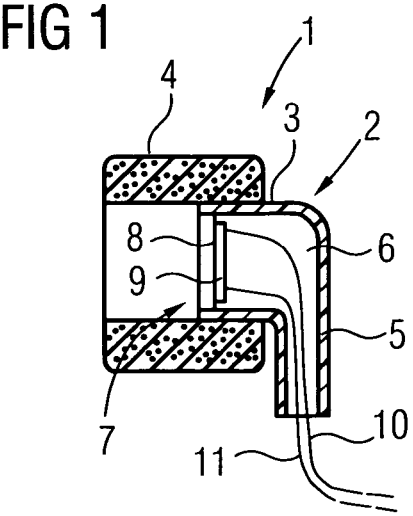
FIG. 1 is a schematic diagram showing an inventive hearing protector of a first embodiment in a sectional view.

FIG. 1 shows an inventive hearing protector 1 of a first embodiment. The hearing protector 1, which is intended to be arranged in an ear as an in-ear headphone, comprises a housing-like adapter 2 which in this case is embodied as angled. It includes a first adapter or retaining section 3 which is cylindrical in shape and serves as a retaining section for an ear pad 4 that is detachably inserted thereon. Also provided is a second adapter section 5 which stands out essentially at right angles and is brought out of the control lines, as is explained further below.

The adapter 2 forms a reception chamber 6 for a sound generating device 7, consisting in this case of an oscillating membrane 8 and a coil 9 directly coupled thereto. Said coil 9 can be embodied as an annular coil having one or more turns and wound onto the oscillating membrane. However, a flat coil having, for example, a meander-shaped structure is also conceivable.

The two control lines 10, 11 which lead to and from the coil 9 to an external signal generating device are brought, coming from the coil 9, into the adapter section 5 and run from the latter to the external signal or control device.

During operation, the coil 9 receives corresponding control signals by way of the control lines 10, 11. Via said control signals in combination with the base magnetic field B0 (shown by way of example in FIG. 4) that always exists during the recording of a magnetic resonance image, an alternating field can be generated via which an oscillation of the oscillating membrane 8 can be effected for the purpose of generating sound signals.

The hearing protector 1 is inserted together with the ear pad 4 directly into the ear or auricle. In this case the ear pad 4, which preferably consists of a soft foam material, though it can also consist of another soft, flexible plastic material, becomes slightly wedged in the ear or auricle, thereby fixing the hearing protector 1 in place. Depending on the length of the adapter 2 or the retaining section 3, this is also situated to some extent in the auricle. This clearly results in an extremely small design overall, and the hearing protector can be integrated almost completely in the auricle. Considering that the auricle region which leads into the ear or auditory canal is very small in dimension, it necessarily means that the diameter of the reception chamber 6 in which the oscillating membrane 8 and the coil 9 are arranged is likewise very small. The oscillating membrane itself is only a few tens of square millimeters in size. The sound generation itself is compatible with the magnetic resonance imaging, since the generated alternating field of the coil 9 is negligible.

Figure 2:
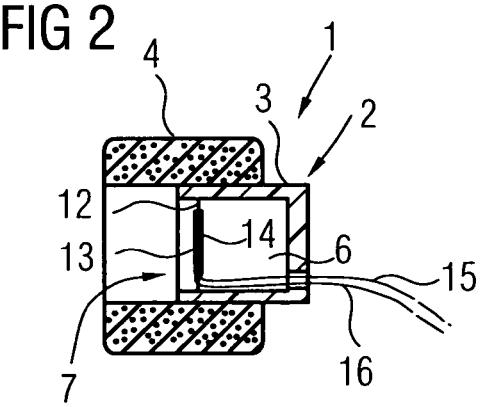
FIG. 2 is a schematic diagram showing an inventive hearing protector of a second embodiment in a sectional view.

A further inventive embodiment of a hearing protector 1 is shown in FIG. 2. An adapter 2 is provided there too, though in this instance it is of elongate shape. It also has a reception chamber 6 for a sound generating device 7, although the latter is a piezoelectric sound generating device. This comprises a middle layer 12 made of a piezoelectric material, on each side of which layer a metal layer 13, 14 is applied. Each metal layer 13 is connected to an external signal generating device via a control line 15, 16. If an alternating voltage is now applied to the two metal layers 13, 14, this leads to a change in the geometry of the piezoelectric layer 12. An oscillation can be generated hereby, with said piezoelectric sound generating device itself acting as an oscillating membrane, which is to say that both the piezoelectric layer 12 and the two metal layers 13, 14 oscillate.

In this case, too, an ear pad 4 is detachably inserted, e.g. by way of a light clamping or latching fastener, onto the adapter 2, which in this instance, like the retaining section 3, has a cylindrical outer shape, such that the ear pad 4 can be replaced without difficulty when necessary.

The piezoelectric sound generating device shown in FIG. 2 is also compatible with the magnetic resonance imaging. The two metal layers 13, 14 are negligible in terms of their interference potential, not least in view of the possibility of positioning the measuring coils closer to the head than has previously been known in the prior art.

Figure 3:
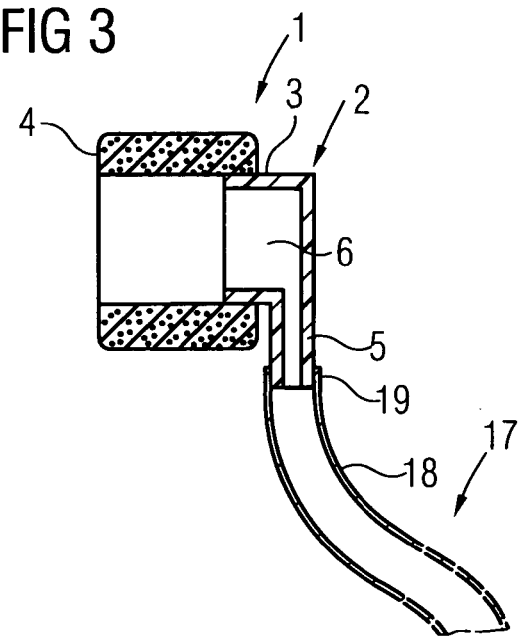
FIG. 3 is a schematic diagram showing an inventive hearing protector of a third embodiment in a sectional view.

A third embodiment of an inventive hearing protector 1 is shown in FIG. 3. Here, too, an adapter 2 is provided which once again is embodied, purely by way of example, in an angled shape. In this instance, too, an ear pad 4 is detachably arranged on the retaining section 3. This time, however, no integrated sound generating device 7 is used, but instead a sound transmitting device 17 in the form of a thin, flexible tube 18 having as small a diameter as possible of only a few millimeters. Said tube 18 leads to an external sound generating device in which the sound signals to be emitted are generated by way of a corresponding transducer. A plug-in section 19, onto which the thin tube 18 is inserted, is embodied on the adapter 2 at the angled section 5. The adapter 2 itself is open, which means that sound waves supplied via the tube 18 enter the chamber 6 by way of the angled section 5 and can be distinguished without difficulty by the wearer.

This hearing protector 1, too, is extremely small, so can be positioned without difficulty in immediate proximity to the head of the patient, fixed in place in the ear by way of the ear pad 4.

Figure 4:
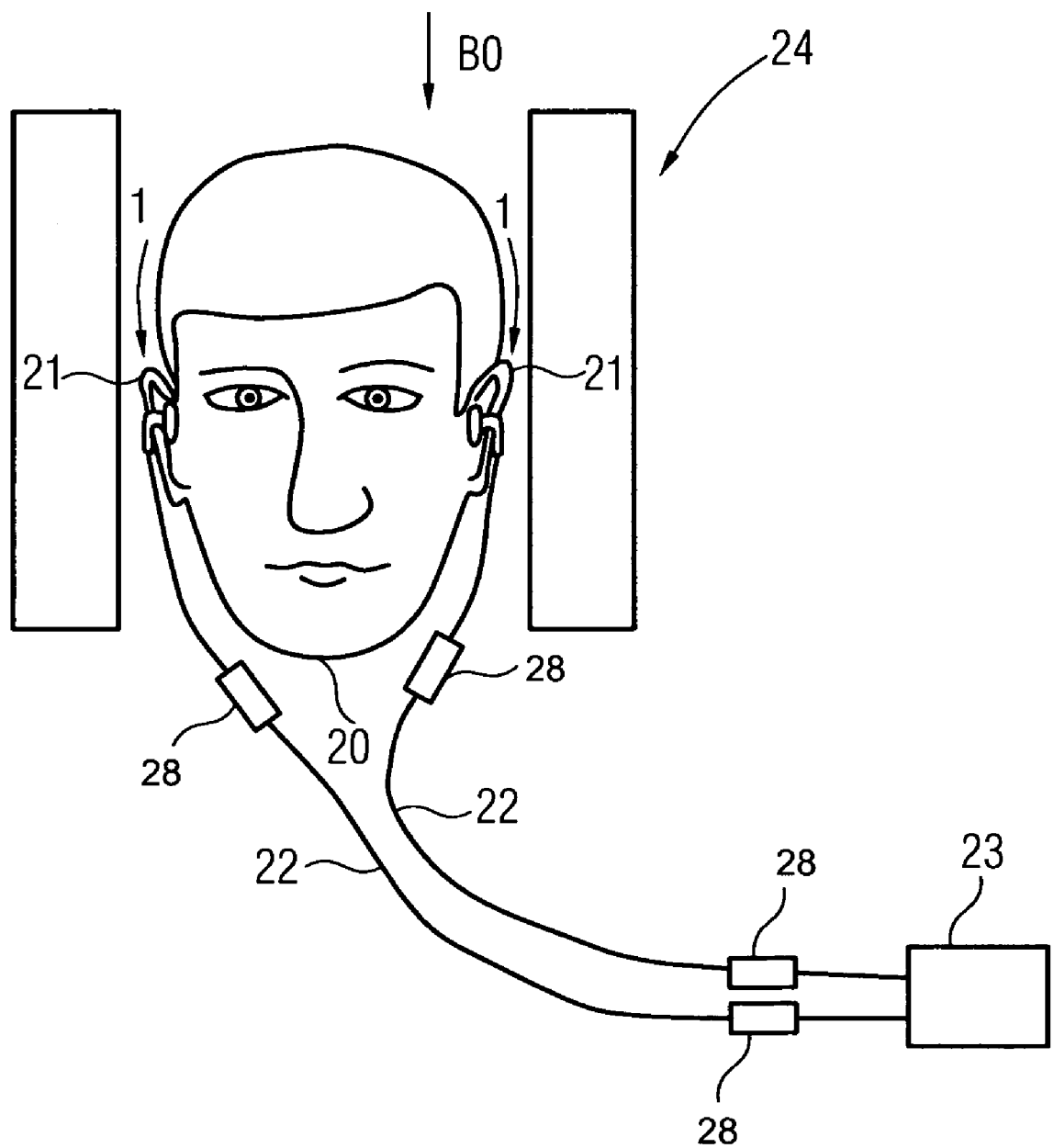
FIG. 4 is a schematic diagram showing a hearing protector being worn in the course of the recording of a magnetic resonance image.

The arrangement of two hearing protectors 1 of said kind during a magnetic resonance imaging session is shown in FIG. 4 in the form of a schematic diagram. The figure shows the head 20 of a patient, with two inventive hearing protectors 1, which of the embodiments described being immaterial, being arranged in the two ears 21. The respective control lines, in this case designated simply by 22, lead to a corresponding control or sound generating device 23 external to the magnetic resonance device.

Also shown is the base magnetic field B0, which is necessary for the operation of a sound generating device 7 comprising a coil together with oscillating membrane, as has been described with reference to FIG. 1. Said base magnetic field B0 plays no role when the other inventive hearing protector embodiments are used.

Also shown is a measuring coil 24, which by way of example is a pure head coil. As can clearly be seen, the head coil 24 can be positioned almost directly against the head 20 of the patient. This means that in the end the respective hearing protector 1 is not limiting with regard to the closeness of the measuring coil 24, as is the case in the prior art with conventional, large-volume hearing protector embodiments which cover the ears overall in the manner of a shell.

As FIG. 4 also shows, it is necessary, when using hearing protectors according to the embodiments shown in FIGS. 1 and 2, in which, that is to say, control signals are transmitted via the control lines 10, 11 and 15, 16 respectively, to integrate sheath wave absorbers 28, depicted optionally in FIG. 4, into the corresponding control lines.

Figure 5:
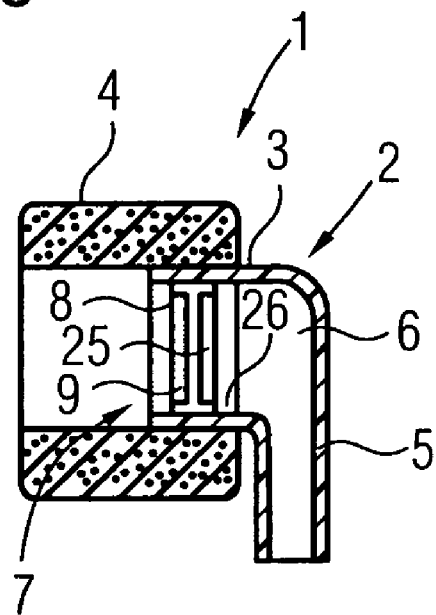
FIG. 5 is a schematic diagram showing an inventive hearing protector of a fourth embodiment in a sectional view.

A further inventive embodiment of a hearing protector 1 is shown in FIG. 5. This essentially corresponds to the embodiment according to FIG. 1, with the same reference numerals designating identical components. In this case, in the interests of greater transparency, the control lines 10 and 11, which are, of course, still present in this arrangement, are no longer drawn in. In contrast to FIG. 1, in addition to the coil 9 connected to the oscillating membrane, the hearing protector 1 includes an identically designed, fixedly mounted compensation coil 25 which is arranged on a carrier element 26 of the adapter 2. The coil 9 and the compensation coil 25 are arranged axially adjacent to each other at a certain distance which is chosen such that the coils 9, 25 just do not touch when the oscillating membrane 8 is at its maximum deflection. In order to generate a compensation field, the compensation coil 25 is supplied with current inversely to the coil 9, with the result that the fields of the two coils essentially cancel each other out and only a slight, rapidly decaying quadrupole stray field remains. The compensation coil 25 therefore compensates for the most part for the field of the coil 9. Furthermore, the resonance or, as the case may be, efficiency of the oscillating membrane 8 is improved as a result of the repelling force between the oscillator coil 9 and the fixedly mounted compensation coil 25.

Figure 6:
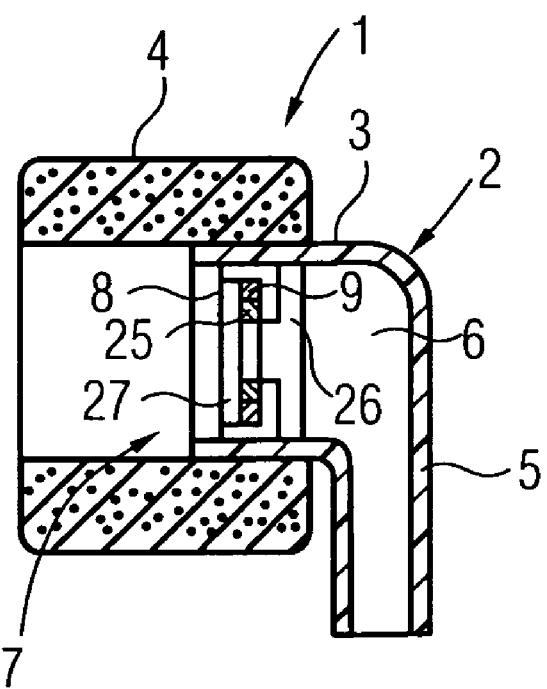
FIG. 6 is a schematic diagram showing an inventive hearing protector of a fifth embodiment in a sectional view.

A further embodiment of an inventive hearing protector 1 having a compensation coil 25 is shown in FIG. 6, where, once again for the sake of clarity, the control lines 10 and 11, which, of course, continue to be present and are also connected to the fixedly mounted compensation coil 25, are not drawn in. In this fifth embodiment, the coil 9 is embodied as an annular coil which is connected to the oscillating membrane 8 by way of a spacer ring 27. In this case the compensation coil 25 is not of identical design to the coil 9, but is also an annular coil having a smaller diameter, such that, as illustrated, it is inserted, fixed to the carrier element 26, into the coil 9 as congruently as possible. A contact with the oscillating membrane 8 while the latter is in oscillation is effectively prevented by means of the spacer ring 27. Alternatively, it can also be provided that an oscillating membrane 8 bulging inwardly toward the ear is used. In order to generate a compensation field compensating for the field of the coil 9, the coil 25 is also supplied inversely with current via the control lines 10, 11. Once again, only a rapidly decaying stray quadrupole field occurs.

It is self-evident that other arrangements, in particular also having a plurality of compensation coils, are also conceivable by means of which a suitable compensation field can be generated.

The inventive hearing protector embodiments, as have been described herein, permit the generation or, as the case may be, transmission of exceptionally distinguishable sound signals. This enables signals such as music or the like that enhance patient comfort to be transmitted in principle during an examination. Nonetheless it is also possible to transmit corresponding instructions, in order, for example, to prompt the patient to take corresponding actions or to transmit possible stimulation signals in the course of a functional imaging session.

The invention claimed is:

1. A hearing protector for protecting a patient undergoing an examination in a magnetic resonance system, comprising:
   an adapter;
   a pad arranged on the adapter that is to be inserted in an ear of the patient; and
   a sound generating device arranged on the adapter that generates sound waves.

2. The hearing protector as claimed in claim 1, wherein the sound generating device comprises a controllable coil connected to an oscillating membrane.

3. The hearing protector as claimed in claim 2, wherein the coil is an annular coil comprising a turn or a flat coil lying in a plane.

4. The hearing protector as claimed in claim 3, wherein a fixedly mounted compensation coil is arranged on the adapter that compensates a magnetic field generated by the coil.

5. The hearing protector as claimed in claim 4, wherein the compensation coil is identical to the coil and is arranged axially adjacent to the coil and can be inversely supplied with a current.

6. The hearing protector as claimed in claim 4, wherein the compensation coil is an annular coil and is arranged coaxially to the coil at least partially inside the coil or enclosing the coil and can be inversely supplied with a current.

7. The hearing protector as claimed in claim 1, wherein the sound generating device comprises a controllable piezoelectric transducer which serves as an oscillating membrane.

8. The hearing protector as claimed in claim 1, wherein a sheath wave absorber is integrated in a control line of the sound generating device.

9. The hearing protector as claimed in claim 1, wherein the pad is detachably fixed to an outside of the adapter.

10. The hearing protector as claimed in claim 1, wherein the adapter has an essentially cylindrical shape.

11. The hearing protector as claimed in claim 1, wherein at least over a third of a length of the adapter is accommodated in the pad.

12. The hearing protector as claimed in claim 1, wherein the adapter has an angled shape and the pad is detachably inserted onto an angled retaining section of the adapter.

* * * * *